United States Patent
Brederlow et al.

(10) Patent No.: US 7,398,671 B2
(45) Date of Patent: Jul. 15, 2008

(54) MICROMECHANICAL SENSOR ELEMENT

(75) Inventors: Ralf Brederlow, München (DE);
Roland Thewes, Gröbenzell (DE)

(73) Assignee: Siemens Aktiengesellschaft (DE)

( * ) Notice: Subject to any disclaimer, the term of this patent is extended or adjusted under 35 U.S.C. 154(b) by 0 days.

(21) Appl. No.: 10/472,632

(22) PCT Filed: Mar. 15, 2002

(86) PCT No.: PCT/DE02/00944

§ 371 (c)(1),
(2), (4) Date: Sep. 19, 2003

(87) PCT Pub. No.: WO02/075296

PCT Pub. Date: Sep. 26, 2002

(65) Prior Publication Data

US 2004/0093947 A1    May 20, 2004

(30) Foreign Application Priority Data

Mar. 19, 2001  (DE) ................................ 101 13 254

(51) Int. Cl.
*G01H 13/00*    (2006.01)
(52) U.S. Cl. .................. 73/24.06; 422/69; 73/61.75
(58) Field of Classification Search .............. 73/580, 73/24.06, 61.75, 61.79; 422/69; 435/287.9
See application file for complete search history.

(56) References Cited

U.S. PATENT DOCUMENTS

| 4,549,427 | A | | 10/1985 | Kolesar, Jr. | |
|---|---|---|---|---|---|
| 4,674,319 | A | * | 6/1987 | Muller et al. | 73/24.01 |
| 4,760,353 | A | | 7/1988 | Perkins | |
| 4,815,843 | A | | 3/1989 | Tienfenthaler et al. | |
| 5,825,119 | A | * | 10/1998 | Shibata et al. | 73/54.24 |
| 5,852,229 | A | * | 12/1998 | Josse et al. | 73/24.06 |
| 5,936,150 | A | * | 8/1999 | Kobrin et al. | 73/24.06 |
| 6,189,367 | B1 | * | 2/2001 | Smith et al. | 73/24.06 |
| 6,837,097 | B2 | * | 1/2005 | Cunningham et al. | 73/24.06 |

FOREIGN PATENT DOCUMENTS

EP    0 072 744 A2    2/1983

(Continued)

OTHER PUBLICATIONS

J. Wang, "Towards Genoelectronics: Electrochemical Biosensing of DNA-Hybridization," Chem. Eur. J., vol. 5, No. 6, 1999.

(Continued)

*Primary Examiner*—John E Chapman
(74) *Attorney, Agent, or Firm*—Altera Law Group, LLC

(57) ABSTRACT

A micromechanical sensor element for recording the bonding of molecules to the micromechanical sensor element. The sensor element having a substrate and at least one electrical terminal. There is also an oscillatable element that is coupled to the electrical terminal in such a manner that an electrical variable that characterizes the oscillation behavior of the oscillatable element may be provided at the electrical terminal. Further, there is a molecule coupling layer, arranged in such a manner that molecules may bond to the molecule coupling layer. The molecule coupling layer is coupled to the oscillatable element in such a manner that bonding of molecules to the molecule coupling layer causes a change in the oscillation behavior of the oscillation element.

5 Claims, 6 Drawing Sheets

FOREIGN PATENT DOCUMENTS

| | | |
|---|---|---|
| EP | 0072744 | 2/1983 |
| JP | 1212105 | 8/1989 |
| JP | 06027703 A | 2/1994 |
| JP | 06027703 B | 2/1994 |
| JP | 09-145583 | 6/1997 |
| WO | WO 89/09938 | 10/1989 |
| WO | WO 98/50773 | 11/1998 |
| WO | 00/66266 | 11/2000 |

OTHER PUBLICATIONS

T. Abe, et al., "One-chip multichannel quartz crystal microbalance (QCM) fabricated by Deep RIE," Sensors and Actuators, Nr. 82, pp. 139-143, 2000.

W.K. Schubert et al., "Chemical sensing with a magnetically-excited flexural plate wave resonator," Electrochemical Society Proceedings, vol. 99-23, pp. 332-335, 1999.

E.A. Wachter et al., "Micromechanical sensors for chemical and physical measurements," Rev. Sci. Instrum. 66 (6), pp. 3663-3667, Jun. 1995.

Günter, Sauerbrey, "Verwendung von Schwingquarzen zur Wägung dünner Schichten und zur Mikrowägung," Zeitschrift für Physik 155, pp. 206-222, 1959. (Concise Statement of Relevance attached hereto).

\* cited by examiner

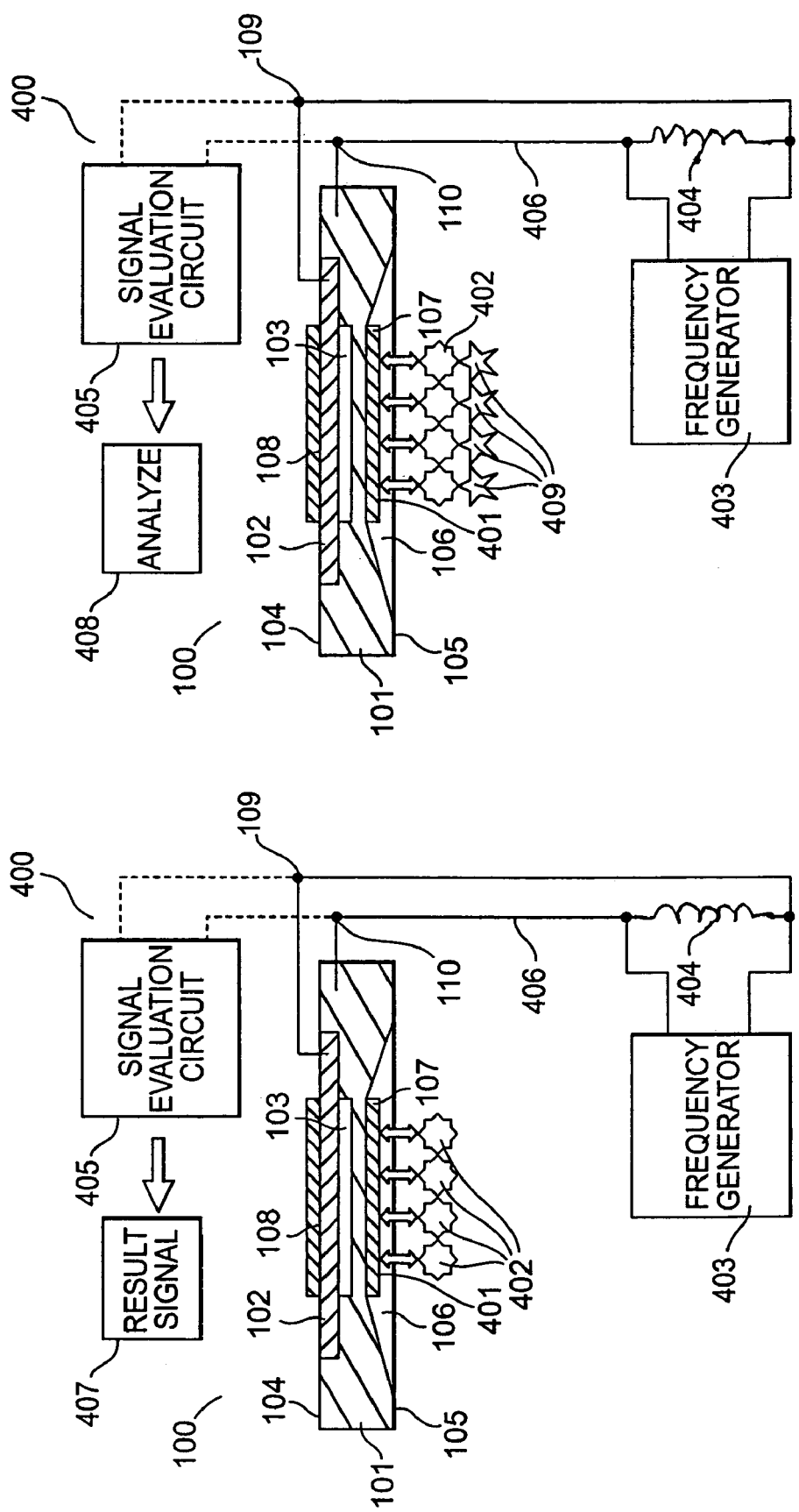

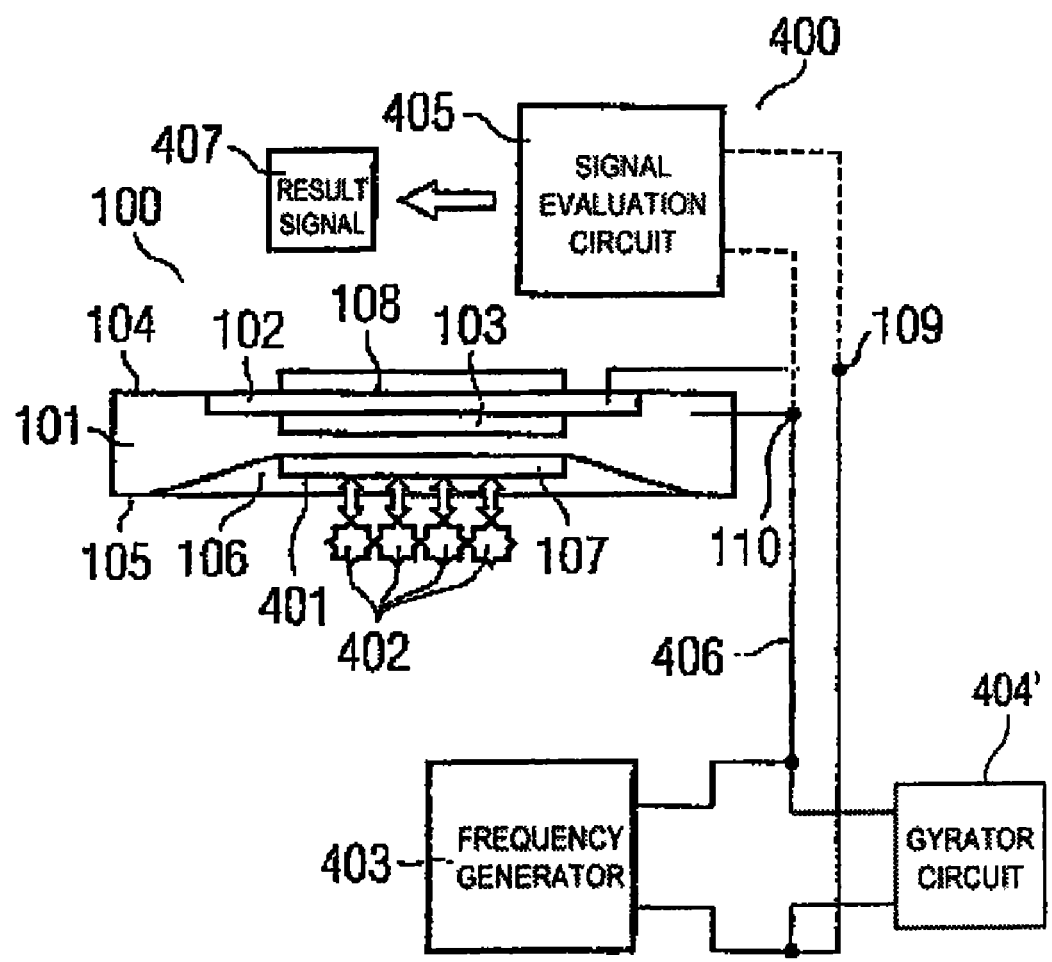

MICROMECHANICAL SENSOR ELEMENT

BACKGROUND OF THE INVENTION

1. Field of the Invention

The invention relates to a micromechanical sensor element.

A chemical reaction can easily be characterized or detected at the interface with a solid body. Therefore, a chemical reaction of this type is often used in chemical and pharmaceutical analysis. Analysis methods of this type are suitable both for large series of tests in pharmaceutical research and for what are known as home-care applications.

2. Description of the Related Prior Art

"J. Wang, Towards Genoelectronics: Electrochemical Biosensing of DNA-Hybridization, Chem. Eur. J., Vol. 5, No. 6, 1999, gives an overview of various methods used to detect chemical bonds at an interface with a solid body."

The various methods used to detect chemical bonds at an interface of a solid body can be substantially divided into four classes of method, namely into optical, electrical, chemical and mass spectroscopy methods.

However, hitherto the analysis of chemical surface reactions has according to every known method been carried out using relatively expensive macroscopic or optical methods, and the evaluation of the data determined by means of discrete electronics.

"Furthermore, Gunther, Use of oscillating crystals for weighing thin films and for micro-weighing, Zeitschrift fur Physik 155, pp. 206-222, 1999, has disclosed what is known as the EACM method (Electrochemical Quartz-Crystal Microbalance method), which also makes use of the fact that the electrically stimulatable resonant frequency of an oscillating crystal which is coated with a metal on two sides has a defined dependency on the interface condition of the metal electrodes (mass change of the oscillating mass) and on their environment (for example the viscosity of a liquid). If a chemical reaction is carried out at the surface of a quartz crystal which has been coated in this manner, the resonant frequency of the system under consideration changes."

"Furthermore, T. Abe et al, One-chip multichannel quarts crystal microbalance (QCM) fabricated by Deep RIE, Sensors and Actuators, No. 82, pp. 139-143, 2000 and WO 89/09938 to Charych, et al., have described QCM arrangements (Quartz-Crystal Microbalance arrangements) and coupling layers for these arrangements."

"W. K. Schubert et al., Chemical Sensing with a magnetically-excited flexural plate wave resonator, Electrochemical Society Proceedings, Vol. 99-23, pp. 332-335, 1999 describes an FPW resonator (Flexural Plate Wave resonator) which is used as a sensor element. In the case of the FPW resonator, the deflection of a membrane and the detection of the frequency change are carried out using electromagnetic means."

"E. A. Wachter et al., Micromechanical sensors for chemical and physical measurements, Rev. Sci. Instrum. 66(6), pp. 3662-3667, June 1995 describes a cantilever as an oscillatable element, with the frequency being detected by optical means."

BRIEF SUMMARY OF THE INVENTION

The invention is based on the problem of providing a micromechanical sensor element which is less expensive to produce than the known sensors.

The problem is solved by the micromechanical sensor element having the features described herein.

A micromechanical sensor element for recording the bonding of molecules to the micromechanical sensor element has a substrate and at least one electrical terminal. Furthermore, there is an oscillatable element, which is coupled to the electrical terminal in such a manner that an electrical variable which characterizes the oscillation behavior of the oscillatable element can be provided at the electrical terminal. Furthermore, there is a molecule coupling layer, which is arranged in such a manner that molecules can bond to the molecule coupling layer. The molecule coupling layer is coupled to the oscillatable element in such a manner that bonding of molecules to the molecule coupling layer causes a change in the oscillation behavior of the oscillatable element, in other words in the impedance of the oscillatable element, preferably the capacitance of the oscillatable element.

The electric circuit may be introduced into the substrate, i.e. may be integrated in the substrate, or may be applied to the substrate.

According to one configuration of the invention, the oscillatable element is introduced into the substrate.

According to a further configuration of the invention, the oscillatable element has an oscillatable membrane and a cavity in the substrate. The oscillatable membrane is arranged in such a manner in relation to the cavity that when it oscillates it can be deflected into and out of the cavity. The oscillatable membrane is coupled to the electrical terminal, so that it is possible, via the oscillatable membrane, to provide an electrical variable which characterizes the oscillation behavior of the oscillatable element to the electrical terminal.

The molecule coupling layer may be made from the same base material as the substrate, for example from silicon or a similar semiconductor element, or from a III-V semiconductor structure or a II-VI semiconductor structure or a metal electrode, for example comprising platinum or gold.

If both the oscillatable membrane and the substrate are made from the same base material, for example are simply doped with different, opposite doping atoms, it is considerably easier to produce a micromechanical sensor element of this type, which can therefore be made significantly less expensive.

According to an alternative configuration of the invention, the oscillatable element is applied to the substrate.

In this case, the oscillatable element may include an oscillatable membrane, which is applied to the substrate in such a manner that a cavity is formed between the oscillatable membrane and the substrate, so that the membrane can be deflected into the cavity and out of the cavity. Likewise according to this exemplary embodiment of the invention, the oscillatable membrane is coupled to the electrical terminal in such a manner that an electrical variable which characterizes the oscillation behavior of the oscillatable element can be provided to the electrical terminal via the oscillatable membrane. Therefore, the oscillatable membrane is coupled to the electrical terminal.

According to this configuration of the invention, it is possible for at least one spacer element to be provided between the substrate and the oscillatable membrane, so that the oscillatable membrane is applied to a surface of the spacer element itself or to a surface of the spacer elements, the spacer element being secured to the substrate on a further surface, on the opposite side from the first surface, of the spacer element, so that on account of the spacer elements the cavity is formed between the substrate and the oscillatable membrane.

This configuration of the invention results in a micromechanical sensor element which can be produced at very low cost.

The cavity may be filled with piezoelectric material. In this configuration of the invention, it is also possible for the piezoelectric material to be used as a spacer element.

This configuration of the invention further improves the accuracy of the micromechanical sensor element.

According to another refinement of the invention, there is provision for a recess to be introduced into that surface of the substrate which is remote from the oscillatable membrane.

Furthermore, the molecule coupling layer may be a layer of metal, i.e. a metal layer, for example comprising platinum, gold or titanium. In principle, the molecule coupling layer can be made from any type of material, depending on the particular application, which is suitable for bonding the corresponding molecule which is to be detected to its surface, for example by means of van der Waals forces or a covalent bond.

In the case of a micromechanical sensor element according to an alternative configuration of the invention, a piezoelectric layer is applied to the substrate, and the molecule coupling layer is applied to the piezoelectric layer. The molecule coupling layer is coupled to a first electrical terminal, and the substrate is coupled to a second electrical terminal, so that, on account of the changing oscillating mass when molecules bond to the molecule coupling layer, the resonant frequency of the unit made up of molecule coupling layer and piezoelectric layer is altered, and this unit is used to provide an electrical variable which characterizes the oscillation behavior of the oscillatable element to the electrical terminals.

According to a further configuration of the invention, a Bragg reflector layer is applied to the substrate beneath the piezoelectric layer. In this case, the Bragg reflector layer itself is responsible for increasing the quality of the piezo-resonator. The Bragg reflector layer is oriented in such a manner that it substantially completely reflects a wave having the resonant frequency of the oscillatable element.

In this context, two layers, which can be arranged on top of one another in a periodically repeating manner, have the maximum possible difference in the propagation speed in a first layer $v_1$ and in a second layer $v_2$ for the sound waves generated by the oscillation. The following apply to the thicknesses of the first layer $d_1$ and the second layer $d_2$ for destructive interference:

$$d_1 = \frac{v_1}{4 \cdot f} \quad \text{where } k = 1, 2, 3, \ldots,$$

$$d_2 = \frac{v_2}{4 \cdot f} \quad \text{where } k = 1, 2, 3, \ldots,$$

where f denotes the frequency of the oscillation which is generated.

According to a further configuration of the invention, there is an electric circuit, which is preferably integrated in the substrate and is coupled to at least one electrical terminal. If there is only one electrical terminal, an analyte located on the micromechanical sensor element evidently acts as a reference potential.

Furthermore, the oscillatable element may be coupled to the electric circuit in such a manner that the oscillation behavior of the oscillatable element can be determined by means of the electric circuit.

For this purpose, the electric circuit may have a frequency generator for generating an actuation signal for the micromechanical sensor element with a predetermined frequency, which actuation signal excites the oscillatable element to oscillate.

Furthermore, it is possible to provide a signal detector, by means of which the amplitude and/or frequency and/or phase with which the oscillatable element oscillates on account of the actuation signal can be determined.

The frequency generator may be configured as a gyrator circuit.

Alternatively, there is an electric circuit arrangement
having a micromechanical sensor element for recording the bonding of molecules to the micromechanical sensor element,
having a reference micromechanical sensor element,
the reference micromechanical sensor element not having any molecules bonded to the reference micromechanical sensor element, and
in which a comparison of the signal provided by the micromechanical sensor element and the reference signal provided by the reference micromechanical sensor element is used to record whether molecules have bonded to the micromechanical sensor element.

The micromechanical sensor element according to the invention is clearly based on the basic principle of the EQCM method described above.

On account of the fact that the electrically stimulatable resonant frequency of an oscillating crystal coated with a metal on two sides has a defined dependency on the interface condition of the metal electrodes and their environment, in the event that a chemical reaction is carried out at the surface of a quartz crystal coated in this manner, the resonant frequency of the oscillatable element and the molecule coupling layer coupled to it is changed.

The change in the amplitude of the excited oscillation of the oscillatable element in a frequency range outside the resonant frequency can also be detected and evaluated.

In this way, it is possible for the chemical reaction to be determined to an electrically detectable change in the resonant frequency and, more generally, as a change in the oscillation properties of the oscillating crystal, generally the oscillation properties of the oscillatable element.

According to the invention, the evident function of the oscillating crystal according to the prior art is taken over by the following:

The membrane or the plurality of membranes.

Since the silicon substrate which is provided in accordance with one configuration of the invention, unlike the quartz crystal, i.e. the crystalline silicon dioxide, which is used in accordance with the prior art, is not a piezoelectric material, although the expected oscillations of the membrane or membranes are weaker, this effect is at least compensated for by the short distances between the individual elements which can be achieved in micromechanics.

In this way, the invention ensures that the micromechanical sensor element, on account of its miniaturization, allows a considerably higher spatial and quantitative resolution compared to the prior art.

Furthermore, the qualitative and quantitative analysis of chemical surface reactions, for example the coupling of deoxyribonucleic acid (DNA) to a gold surface by means of sulfur bonds or to a silicon surface by means of chlorine bonds, is automated. This leads to a considerable reduction in the costs during the production of a micromechanical sensor element and to an improvement in the analysis accuracy of a micromechanical sensor element of this type.

A piezoelectric layer which is applied directly and to whose (metallic) surface remote from the electric circuit a metal layer which is optionally to be provided in addition and to which the molecules can bond is applied.

In this context, it should be noted that the molecule coupling layer may be formed both by the substrate itself, if the substrate is made from a material to which the molecules can bond, and by an independent layer applied to the substrate.

This situation clearly represents an integrated oscillating quartz crystal; the material of the piezoelectric layer does not necessarily have to be quartz. By way of example, lead zirconium titanate (PZT) can be used as material for the piezoelectric layer.

At least one side of the membrane or membranes or of the additional metal layer forms the surface of the solution which is to be analyzed, i.e. the contact surface for the molecules which are to be bonded to the surface in question.

The bonding of molecules to this surface causes the amplitude or frequency of the oscillation of the oscillatable element to change.

For this purpose, the membrane or membranes can be evaporation-coated with a thin metal layer, the molecule coupling layer. This has an amplifying effect with regard to the change in the resonant oscillations.

The oscillation of the oscillatable element can be excited by the application of an AC voltage between two electrodes which are connected to the two electrical terminals of the micromechanical sensor element.

One electrode in this case forms a membrane or the metalization beneath that side of the piezoelectric layer which faces the integrated circuit, in the situation in which the electric circuit is integrated in the substrate, while the other electrode is the contact surface or the solution applied to the micromechanical sensor element, i.e. the analyte itself.

The invention clearly provides a very inexpensive and very simple interface with the electronics, since, using the option of silicon microelectronics in accordance with one configuration of the invention, signal processing and/or evaluation of the data determined is carried out directly at the location of the sensor, i.e. in the micromechanical sensor element itself, that is to say on-chip.

This eliminates the need for long connection lines and considerably increases the resolution of the micromechanical sensor element.

In electronic terms, the change in the oscillation frequency caused by the mass and viscosity change of the membrane, or in general of the oscillatable element, corresponds to a change in the membrane capacitance or the capacitance of the oscillatable element.

Since, by way of example, the resonant frequency of a resonant circuit is a function of the resonant circuit capacitance, the change in this frequency is also a measure of the change in the mass at the membrane.

In this context, it should be noted that the mass which actually oscillates is small compared to the overall mass of the micromechanical sensor element, so that a relatively major relative change in the mass can be achieved and detected.

According to a further configuration of the invention, there is provision for two different resonant frequencies to be compared with one another, namely a first resonant frequency, in a state in which the micromechanical sensor element has not yet been brought into contact with an analyte in which the molecules to be bonded may be present, and in a second state, after the sensor element has been brought into contact with the analyte in such a manner that any molecules contained in the analyte have been able to bond to the contact surface of the micromechanical sensor element. On account of the relative comparison of two frequencies, the result of the evaluation is robust with regard to manufacturing tolerances and interference.

Moreover, arranging micromechanical sensor elements which are of the same type or are sensitive to different reactions so as to form a set of sensors allows positionally resolved measurement with a spatial accuracy which is limited only by the minimum possible size of the membranes which can usefully be employed from the metrological or lithographic aspect.

Therefore, simultaneous analysis of a plurality of chemical reactions can also be achieved both by simultaneous detection of a plurality of oscillation modes and by different surface preparations of the micromechanical sensor elements which are included in the set of sensors.

Furthermore, in a matrix arrangement of the micromechanical sensor elements in the set of sensors, the distribution of the signals which are used to actuate the corresponding oscillatable elements and to excite them to vibrate on the different sensors, i.e. on the different micromechanical sensor elements, also makes it possible to work out changes in oscillation properties in the entire volume of the analyte which has been applied to the overall set of sensors.

If these changes in the oscillation properties are characteristic of a chemical reaction in the analyte, i.e. in the solution, detection of chemical reactions of this type in the solution volume is also possible.

According to a further configuration of the invention, by means of further elements used in motive micromechanics, for example by means of micromechanical pumps and micromechanical locks, there is provision for different solutions to be transported, in a temporal sequence which is suitable for analysis, directly to the micromechanical sensor element or to the micromechanical sensor elements, thereby further increasing the degree of automation.

Furthermore, the invention provides a sensor array having a plurality of micromechanical sensor elements.

BRIEF DESCRIPTION OF THE DRAWINGS

Exemplary embodiments of the invention are illustrated in the figures and are explained in more detail below. In the figures:

FIGS. 4a and 4b illustrate the operational principle of the micromechanical sensor element from FIG. 1 with a parallel resonant circuit as electric circuit for actuating and evaluating the micromechanical sensor element before bonding of molecules has taken place (FIG. 4a) and after bonding of molecules has taken place (FIG. 4b);

FIG. 1 shows a micromechanical sensor element 100 in accordance with a first exemplary embodiment of the invention.

DETAILED DESCRIPTION OF THE INVENTION

Figure 1:
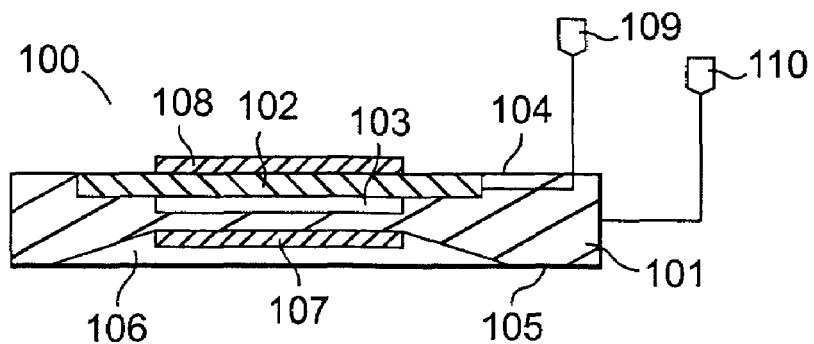
FIG. 1 shows the basic structure of a micromechanical sensor element according to a first exemplary embodiment of the invention.

The micromechanical sensor element 100 has a substrate 101 made from silicon, in which an electric circuit (not shown) is integrated.

The substrate 101, for example a silicon wafer, is p-doped.

A membrane 102, likewise made from silicon, in this exemplary embodiment n-doped, is embedded in the substrate 101.

Furthermore, a cavity, also referred to below as intermediate space 103, is introduced into the substrate 101, and the membrane 102 is applied above it over the entire surface, in such a manner that the entire cavity 103 is covered by the membrane 102.

According to this exemplary embodiment, the cavity 103 is filled with air, or alternatively, for example, with piezoelectric material with a suitable orientation.

The micromechanical sensor element has a front-side surface 104 and a rear-side surface 105.

A further cavity 106 is etched from the rear into the rear-side surface 105. A first metal layer 107 is applied in the further cavity 106 and to the etched-away surface of the substrate 101.

A region of the substrate 101 is provided between the metal layer 107 and the intermediate space 103.

Furthermore, a further metal layer 108 is applied to the front-side surface 104 of the substrate 101.

A change in frequency or change in amplitude, which is described below, is amplified by means of the metal layers 107, 108.

The metal layers 107, 108, which in this exemplary embodiment are made from gold, are used for capture molecules to be coupled to, in accordance with this exemplary embodiment DNA capture molecules, or in general for any desired molecules to be coupled to, in accordance with this exemplary embodiment molecules of macromolecular biopolymers.

The bonding takes place in accordance with the gold-sulfur bonding.

The term macromolecular biopolymers is to be understood as meaning, for example, proteins or peptides or else DNA strands of in each case a predetermined sequence.

If the macromolecular biopolymers to be recorded are proteins or peptides, the capture molecules are ligands, for example active substances with possible bonding activity which bond the proteins or peptides to be recorded to the coupling layer in question, on which the corresponding ligands are arranged.

Suitable ligands include enzyme agonists or enzyme antagonists, pharmaceuticals, sugars or antibodies or any molecule which has the ability to specifically bond proteins or peptides.

In the context of this description, a probe molecule is to be understood as meaning both a ligand and a DNA probe molecule.

A first terminal 109 is electrically coupled to the membrane 102. A second electrical terminal 110 is electrically coupled to the substrate 101.

Figure 2:
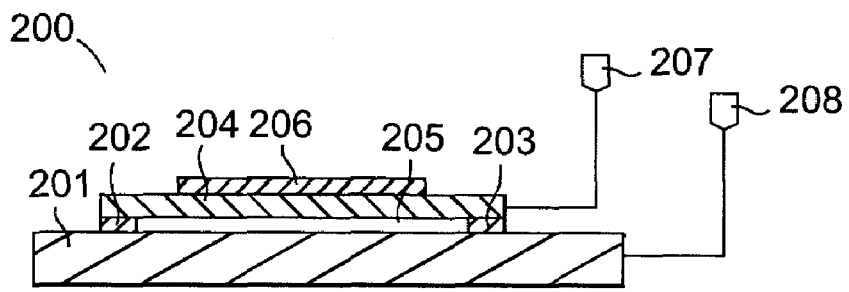
FIG. 2 shows the basic structure of a micromechanical sensor element according to a second exemplary embodiment of the invention.

FIG. 2 shows a micromechanical sensor element 200 in accordance with a second exemplary embodiment of the invention.

The micromechanical sensor element 200 likewise has a substrate 201 made from silicon, in accordance with this exemplary embodiment likewise p-doped.

Spacer elements, according to the present exemplary embodiment webs 202, 203, which serve as spacers between the first substrate 201 and a membrane 204 applied to the webs 202, 203, are provided on the substrate 201.

Also in accordance with the second exemplary embodiment, the membrane 204 is made from n-doped silicon.

The spacers 202, 203 evidently form a closed periphery which is completely covered by the membrane 204, so that an intermediate space 205, which is filled with air or with piezoelectric material of suitable orientation, is formed.

A metal layer 206 of gold is applied to the membrane 204 for the purpose of bonding DNA capture molecules, by means of which any DNA molecules with a complementary sequence contained in an analyte are bonded.

The membrane 204 is electrically coupled to a first electrical terminal 207, and the substrate 201 is electrically coupled to a second electrical terminal 208.

Figure 3A:
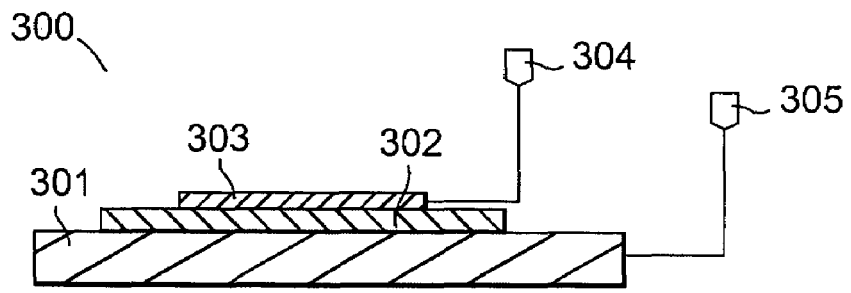
FIGS. 3a and 3b show the basic structure of a micromechanical sensor element in accordance with a third exemplary embodiment of the invention (FIG. 3a) and in accordance with a fourth exemplary embodiment of the invention (FIG. 3b)

FIG. 3a shows a micromechanical sensor element 300 in accordance with a third exemplary embodiment of the invention.

The micromechanical sensor element 300 has a substrate 301 made from p-doped silicon and a piezoelectric layer 302 applied directly to the substrate.

A metal layer of gold 303, which is electrically coupled to a first terminal 304, is applied to the piezoelectric layer 302.

Furthermore, the substrate 301 is electrically coupled to a second electrical terminal 305.

According to this exemplary embodiment, therefore, the metal layer 303 is directly connected to the piezoelectric layer 302, together, according to this exemplary embodiment, forming the oscillatable element.

Figure 3B:
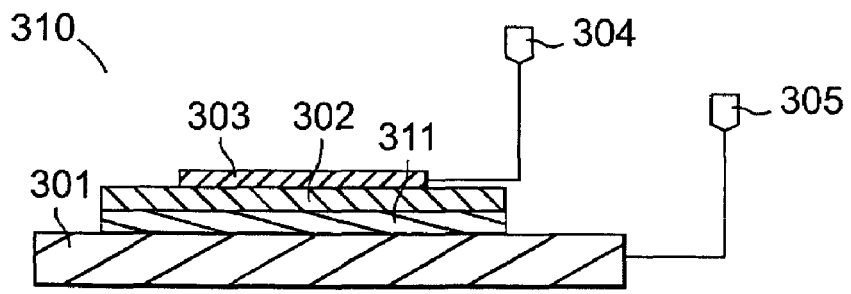

FIG. 3b shows a micromechanical sensor element 310 in accordance with a fourth exemplary embodiment of the invention.

The micromechanical sensor element 310 has a substrate 301 made from p-doped silicon and a Bragg reflector layer 311 applied direct to the substrate. The oscillation quality is considerably increased by means of the Bragg reflector layer 311, which acts as a Bragg reflector and has the corresponding structure.

According to this exemplary embodiment, the piezoelectric layer 302 is applied to the Bragg reflector layer 311.

A metal layer of gold 303, which is electrically coupled to a first terminal 304, is applied to the piezoelectric layer 302.

Furthermore, the substrate 301 is electrically coupled to a second electrical terminal 305.

According to this exemplary embodiment, therefore, the metal layer 303 is directly connected to the piezoelectric layer 302, together, according to this exemplary embodiment, forming the oscillatable element.

FIG. 4a shows the micromechanical sensor element 100 in accordance with the first exemplary embodiment, in which DNA capture molecules 402 are covalently bonded, i.e. immobilized, to an exposed surface 401 of the first metal layer 107 by means of gold-sulfur coupling.

The micromechanical sensor element 100 is coupled to a frequency generator 403, in accordance with this exemplary embodiment optionally connected in parallel with an inductor 404, via the first terminal 109 and the second terminal 110.

As an alternative to the inductor 404, it is also possible to use a gyrator circuit 404' (see FIG. 4c).

Furthermore, a signal evaluation circuit 405 is coupled to the electrical terminals 109, 110.

The resonant frequency of the micromechanical sensor element 100 is determined by means of the signal evaluation circuit 405.

This is effected by the application of an actuation signal 406 to the micromechanical sensor element 100 and corresponding tapping of the resulting frequency at which the membrane 102 of the micromechanical sensor element 100 oscillates.

The signal evaluation unit 405 provides, as the result, the amplitude and phase, or in general terms the resonant frequency, as result signal 407, in accordance with the state shown in FIG. 4a in the situation in which as yet no hybridization of the DNA capture molecules 402 with DNA strands having a complementary sequence to the sequence of the DNA capture molecules has occurred.

In accordance with this exemplary embodiment, the overall evaluation circuit 400, i.e. the frequency generator 403 and the signal evaluation circuit 405 and the inductor 404, is integrated in the substrate 101, i.e. the evaluation circuit is produced on-chip.

In FIG. 4a, the evaluation circuit is arranged outside the chip purely to simplify the explanation of the operating principle.

FIG. 4b shows the micromechanical sensor element 100 for the situation in which an analyte has been brought into contact, in such a manner that DNA strands 409 which are present in the analyte can hybridize with the DNA capture molecules 402.

This state is illustrated in FIG. 4b.

When hybridization of DNA strands 408 to the DNA capture molecules 402 has taken place, actuating the micromechanical sensor element 100 by the actuation signal 406 results in a resonant frequency 408 which differs from the resonant frequency 407 of the micromechanical sensor element 100 with unbonded DNA capture molecules 402 being detected as the result signal.

Therefore, in accordance with these exemplary embodiments, a change in the resonant frequency of the micromechanical sensor element 100 when DNA molecules have bonded or not bonded to the DNA capture molecules 402 causes a change in the resonant frequency of the membrane and the intermediate space 103, or in general terms of the oscillatable element of the micromechanical sensor element 100, to be detected.

Figure 5:
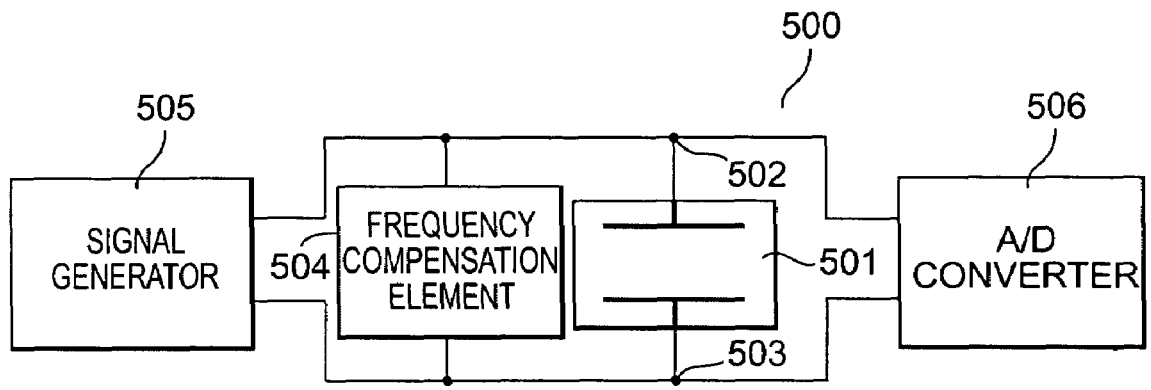
FIG. 5 shows a block diagram of an electric evaluation circuit in accordance with a first exemplary embodiment of the invention for determining the resonant frequency of the micromechanical sensor element.

FIG. 5 shows the general inventive principle in the form of a block diagram for determining the resonant frequency.

A micromechanical sensor element 501, which has the structure of a micromechanical sensor element of one of the exemplary embodiments described above, is connected in parallel, via its two electrical terminals 502, 503, with a frequency compensation element 504, which may be configured as an active frequency compensation element or else as a passive frequency compensation element.

A signal generator 505 is connected to the electrical terminals 502, 503, and is energized so as to excite oscillation in order to generate an electric signal which actuates the micromechanical sensor element, with the result that in general terms a resonant circuit is realized.

Furthermore, an analog/digital converter 506, or alternatively a frequency counter and a digital signal-processing unit, is connected to the electrical terminals 502, 503.

Figure 6:
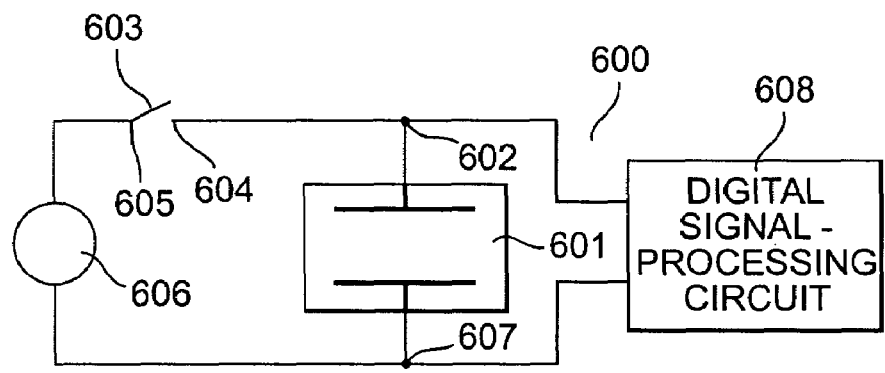
FIG. 6 shows a block diagram of an electric evaluation circuit in accordance with a second exemplary embodiment of the invention for determining the transient response of the micromechanical sensor element.

FIG. 6 shows a block diagram 600 illustrating one possible way of realizing an evaluation circuit for determining the transient response of the micromechanical sensor element 601, which is configured in accordance with the micromechanical sensor element of one of the exemplary embodiments described above.

A switch 603 is connected in series with a first terminal 602 of the micromechanical sensor element 601, a first terminal 604 of the switch being coupled to the first electrical terminal 602 and a second terminal 605 of the switch 603 being coupled to a first terminal of a voltage source 606, the other terminal of which is coupled to the second electrical terminal 607 of the micromechanical sensor element.

Furthermore, an analog/digital converter or a frequency counter and a digital signal-processing circuit 608 is connected in series with the electrical terminals 602, 607.

Figure 7:
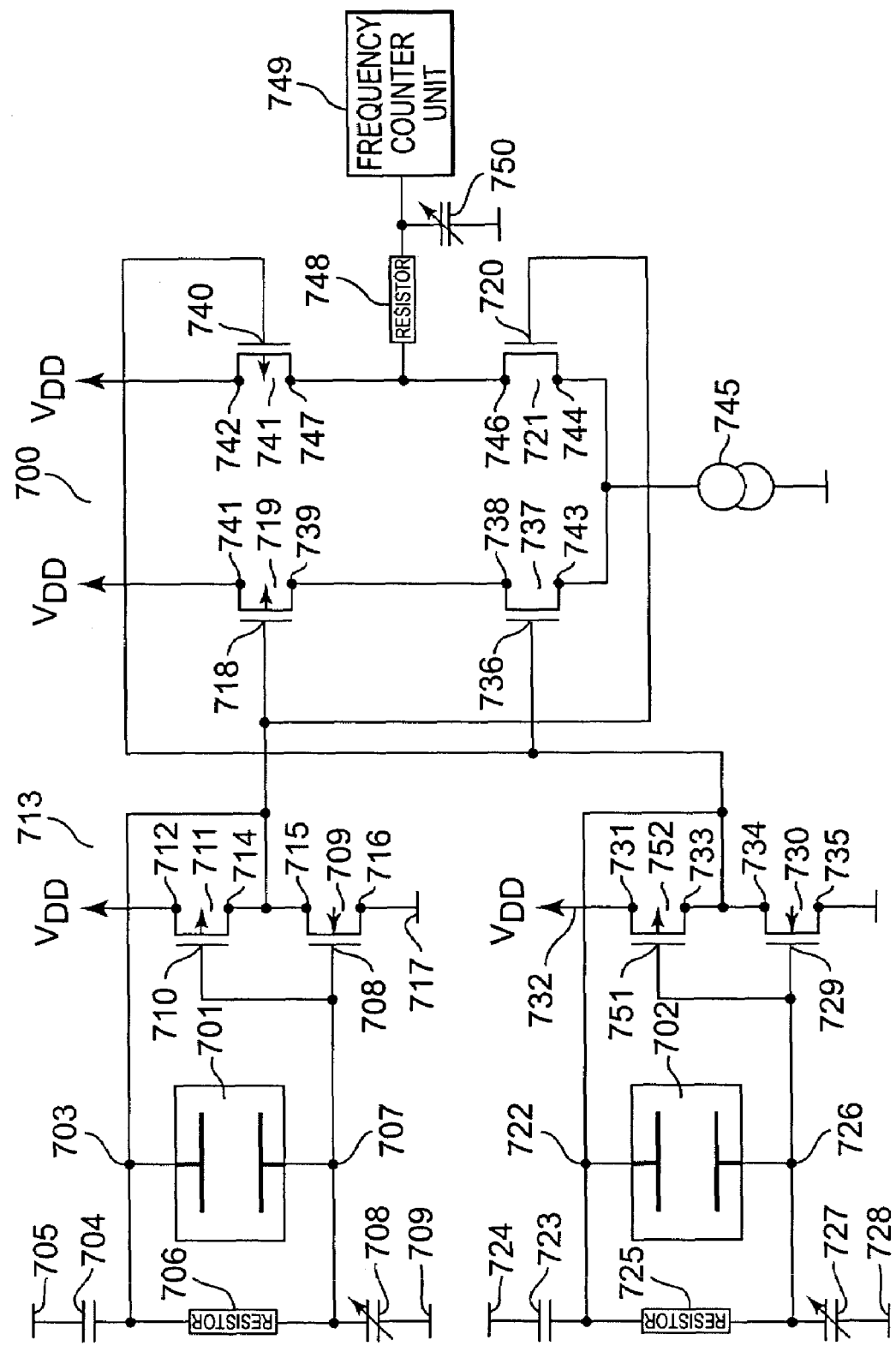
FIG. 7 illustrates the electric evaluation circuit from FIG. 5 in CMOS technology.

FIG. 7 shows an electric circuit 700 for the electrical evaluation of the signals generated by the micromechanical sensor elements in order to determine the resonant frequency, i.e. the electric evaluation circuit 700, realized in CMOS technology.

A first micromechanical sensor element 701 and a second micromechanical sensor element 702 as reference sensor element are provided in the electric circuit 700.

According to this exemplary embodiment, the second micromechanical sensor element 702 is not brought into contact with an analyte, i.e. the DNA capture molecules applied to the second micromechanical sensor element are always unbonded.

A first electrical terminal 703 of the first micromechanical sensor element 701 is coupled to a ground terminal 705 via a capacitor 704 and to a second electrical terminal 707 of the first micromechanical sensor element 701 via an electrical resistor 706.

The second electrical terminal 707 is coupled to the ground potential 709 via a second capacitor 708, the capacitance of which, according to this exemplary embodiment, can be changed.

Furthermore, the gate terminal 708 of a first transistor 709 (NMOS field-effect transistor) and the gate terminal 710 of a second transistor 711 (PMOS field-effect transistor) are coupled to the second electrical terminal 707, the drain terminal 712 of the second transistor 711 being coupled to the operating potential VDD 713 and the source terminal 714 of the second transistor 711 being coupled to the drain terminal 715 of the first transistor 709.

The source terminal 716 of the first transistor 709 is coupled to the ground potential 717.

The source terminal 714 of the second transistor and the drain terminal 715 of the first transistor 709 are also coupled to the gate terminal 718 of a third transistor 719 and to the gate terminal 720 of a fourth transistor 721.

A first electrical terminal 722 of the second micromechanical sensor element 702 is coupled to the ground potential 724 via a further capacitor 723 and is coupled to the second electrical terminal 726 of the micromechanical sensor element 702 via a second electrical resistor 725 and to the ground potential 728 via a capacitor 727 whose capacitance can be changed.

The second electrical terminal 726 of the second micromechanical sensor element 702 is coupled to the gate terminal 751 of a fifth transistor 752 and to the gate terminal 729 of a sixth transistor 730. The drain terminal 731 of the fifth transistor 752 is coupled to the operating potential VDD 732, and the source terminal 733 of the fifth transistor 751 is coupled to the drain terminal 734 of the sixth transistor 730.

The source terminal 735 of the sixth transistor 730 is grounded.

The source terminal 733 of the fifth transistor 728 and the drain terminal 734 of the sixth transistor 730 are therefore coupled to one another and to the gate terminal 736 of a seventh transistor 738, the drain terminal 738 of which is coupled to the source terminal 739 of the third transistor 719.

Furthermore, the gate terminal 736 of the seventh transistor 737 is coupled to the gate terminal 740 of an eighth transistor 741.

The first terminal 703 of the first micromechanical sensor element 701 is, furthermore, coupled to the gate terminal 718 of the fifth transistor 719.

The drain terminal 741 of the third transistor 719 and the drain terminal 742 of the eighth transistor 741 are coupled to the operating potential VDD.

The source terminal 743 of the seventh transistor 737 is coupled to the source terminal 744 of the fourth transistor 721 and to a current source 745.

The drain terminal 746 of the fourth transistor 721 is coupled to the source terminal 747 of the eighth transistor 740 and, via an electrical resistor 748, to a frequency counter unit 749 and a digital signal processing circuit, with a capacitor 750 connected in parallel.

Figure 8:
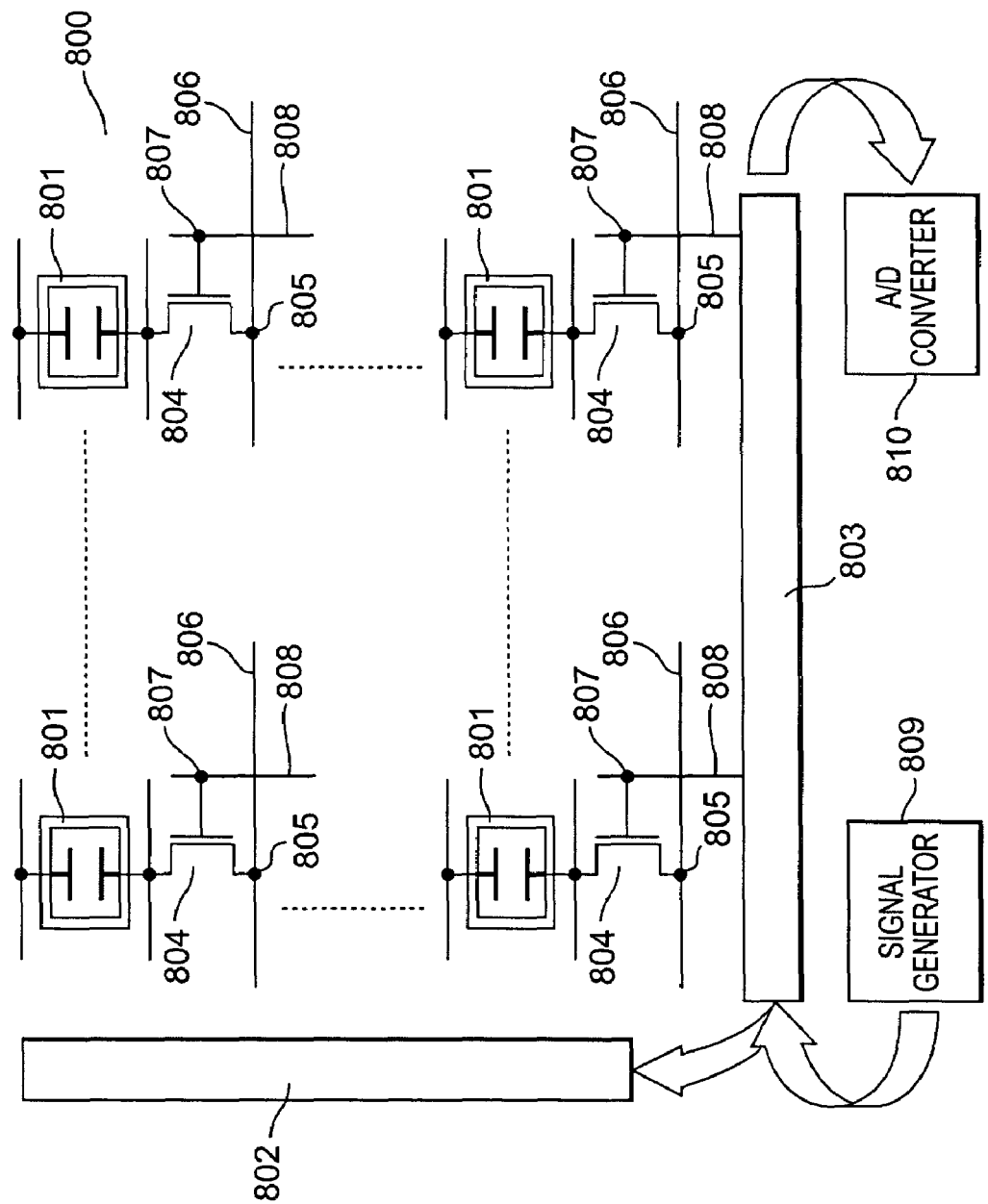
FIG. 8 illustrates a set of sensors having a multiplicity of micromechanical sensor elements arranged to form a matrix.

FIG. 8 shows a set of sensors 800 having a multiplicity of micromechanical sensor elements 801 which are arranged in a matrix arrangement, i.e. in rows and columns, and can be actuated and read out by means of a conventional row decoder 802 and a column decoder 803 via actuation transistors 804, which are each connected in series with the corresponding micromechanical sensor element 801, in each case the source terminal 805 being coupled via a row line to the source terminals 805 of all the transistors belonging to the same row, and being coupled to the row decoder 802 via the respective row line 806.

The gate terminals 807 are coupled to the column decoder 803 via column lines 808. A signal generator 809 is coupled to the column decoder 803 in order to actuate the respective gate terminals 807 of the actuation transistors 804.

Furthermore, an analog/digital converter 810 and a digital signal processing circuit are coupled to the column decoder 803 in order to read out the oscillation signals supplied by the micromechanical sensor element which is in each case selected.

The invention can clearly be seen to reside in an on-chip combination of microelectronics and an arrangement for chemical analysis methods based on changes in mechanical oscillations.

In this context, it should be noted that the respective arrangement may furthermore be provided with additional micromechanical pumps, passages and locks, so that a complete analysis system which includes one or a multiplicity of micromechanical sensor elements is formed.

The invention claimed is:

1. A micromechanical sensor element for recording the bonding of molecules to the micromechanical sensor element, comprising:
    a substrate;
    at least one electrical terminal;
    an oscillatable element applied to the substrate, wherein the oscillatable element is secured to the substrate at least along a closed periphery and is coupled to a first of the at least one electrical terminal in such a manner that an electrical variable which characterizes the oscillation behavior of the oscillatable element is provided at the first of the at least one electrical terminal, wherein the oscillatable element comprises an oscillatable membrane, which is applied to the substrate in such a manner that a cavity is formed between the oscillatable membrane and the substrate, so that the membrane can be deflected into the cavity, wherein the oscillatable membrane is coupled to the first of the at least one electrical terminal, wherein at least one spacer element is provided between the substrate and the oscillatable membrane, and wherein the cavity is filled with piezoelectric material;
    a molecule coupling layer, which is oriented in such a manner that molecules can bond to the molecule coupling layer;
    the molecule coupling layer being coupled to the oscillatable element in such a manner that bonding of molecules to the molecule coupling layer can cause a change in the resonant frequency of the oscillatable element; and
    an electric circuit for determining the oscillation behavior of the oscillatable element, wherein
    the electric circuit is coupled to the oscillatable element via at least the first of the at least one electrical terminal, and wherein
    the electric circuit comprises means for generating an actuation signal with a predetermined frequency, by means of which actuation signal the oscillatable element is excited into oscillation; a feedback mechanism that feeds a signal based on an output of the oscillatable element back into the oscillatable element; and means for detecting and/or evaluating the change in the resonant frequency of the oscillatable element caused by the bonding of molecules to the molecule coupling layer, and wherein
    the electric circuit is integrated in the substrate or applied to the substrate of the micromechanical sensor element.

2. The micromechanical sensor element as claimed in claim 1, in which the oscillatable membrane is made from the same base material as the substrate.

3. The micromechanical sensor element as claimed in claim 1, in which a recess is introduced into that surface of the substrate which is remote from the oscillatable membrane.

4. The micromechanical sensor element as claimed in claim 1, in which the means for generating the actuation signal comprises a frequency generator; and
    in which the means for detecting and/or evaluating the change in the resonant frequency of the oscillatable element comprises a signal detector.

5. The micromechanical sensor element as claimed in claim 4, further comprising the frequency generator being connected in parallel with an inductor or a gyrator circuit.

* * * * *